US005750348A

United States Patent [19]
Larner

[11] Patent Number: 5,750,348
[45] Date of Patent: May 12, 1998

[54] METHOD FOR DETECTING INSULIN RESISTANCE

[75] Inventor: Joseph Larner, Charlottesville, Va.

[73] Assignee: The University of Virginia Patents Foundation, Charlottesville, Va.

[21] Appl. No.: 273,099

[22] Filed: Jul. 8, 1994

Related U.S. Application Data

[63] Continuation-in-part of Ser. No. 953,708, Sep. 30, 1992, Pat. No. 5,427,956, which is a continuation of Ser. No. 870,771, Apr. 21, 1992, Pat. No. 5,183,764, which is a continuation of Ser. No. 476,953, Feb. 8, 1990, abandoned, which is a continuation-in-part of Ser. No. 320,485, Mar. 8, 1989, abandoned.

[51] Int. Cl.$^6$ .......................... G01N 30/72; G01N 33/48; G01N 33/53

[52] U.S. Cl. ...................... 435/7.1; 435/23; 436/131; 436/161; 436/173; 436/518; 436/536; 436/811

[58] Field of Search .................... 435/7.1, 23; 436/131, 436/536, 161, 173, 811, 518

[56] References Cited

U.S. PATENT DOCUMENTS

| | | | |
|---|---|---|---|
| 4,446,064 | 5/1984 | Larner et al. | 260/112 |
| 4,735,936 | 4/1988 | Siren | 514/103 |
| 4,797,390 | 1/1989 | Siren | 514/103 |
| 4,801,597 | 1/1989 | Stacpoole et al. | 514/332 |
| 4,839,466 | 6/1989 | Saltiel | 530/395 |
| 4,906,468 | 3/1990 | Saltiel | 424/85.8 |
| 5,019,566 | 5/1991 | Siren | 514/103 |
| 5,023,248 | 6/1991 | Siren | 514/103 |
| 5,091,596 | 2/1992 | Kennington et al. | 568/833 |
| 5,183,764 | 2/1993 | Kennington et al. | 436/131 |
| 5,427,956 | 6/1995 | Kennington et al. | 436/131 |

FOREIGN PATENT DOCUMENTS

| | | |
|---|---|---|
| 0 179 439 | 4/1986 | European Pat. Off. |
| 0 359 257 | 3/1990 | European Pat. Off. |

OTHER PUBLICATIONS

Cheng, K. et al., "Studies on the Insulin Mediator. II. Separation of Two Antagonistic Biologically Active Materials from Fraction II," *Diabetes* 29(8):659–661 (1980).

Cheng, K. and Larner, J., "Intracellular Mediators of Insulin Action," *Ann. Rev. Physiol.* 47:405–424 (1985).

Cheng, K. and Larner, J., "Unidirectional Actions of Insulin and $Ca^{2+}$-dependent Hormones on Adipocyte Pyruvate Dehydrogenase," *J. Biol. Chem.* 260(9):5279–5285 (1985).

Clements, Jr., R.S. et al., "Myo–inositol Metabolism in Diabetes Mellitus: Effect of Insulin Treatment," *Diabetes* 26(3):215–221 (1977).

Craig, J.W. et al., "Chiroinositol Deficiency and Insulin Resistance," *Molecular Biology of Diabetes, Part II*, ch. 17, Humana Press Inc.: Totowa, NJ (1994).

Greene, D.A. et al., "Effects of Insulin and Dietary Myo-inositol on Impaired Peripheral Motor Nerve Conduction Velocity in Acute Streptozotocin Diabetes," *J. Clin. Invest.* 55:1326–1336 (1975).

Greene, D.A. and Lattimer, S.A., "Impaired Rat Sciatic Nerve Sodium–Potassium Adenosine Triphosphatase in Acute Streptozocin Diabetes and its Correction by Dietary Myo–inositol Supplementation," *J. Clin. Invest.* 72:1058–1063 (1983).

Huang, L.C. et al., "Carbohydrate Constituents of a Putative Insulin Mediator Acting on Mitochondrial Pyruvate Dehydrogenase," *FASEB J.* Abstract 1626:A576 (1988).

Huang, L.C. et al., "Chiroinositol Deficiency and Insulin Resistance. III. Acute Glycogenic and Hypoglycemic Effects of Two Inositol Phosphoglycan Insulin Mediators in Normal and Streptozotocin–Diabetic Rats in Vivo," *Endocrinology* 132(2):652–657 (1993).

Kennington, A.S. et al., "Analysis of Optical Isomers of Chiro–Inositol in Biological Samples," *J. Cell Biochem. Suppl.* O (13 part A) Abstract B406:142 (1989).

Kennington, A.S. et al., "A Simple Procedure for the Preparation and Purification of the Oligosaccharide Components of the Glycosyl–phosphatidylinositol Anchor of Membrane Proteins," *Analytical Biochem.* 181:1–5 (1989).

Larner, J., "Insulin Mediator—Fact or Fancy?" *J. Cyclic Nucleotide Res.* 8(5):289–296 (1982).

Larner, J. et al., "Insulin Mediators and Their Control of Metabolism through Protein Phosphorylation," *Rec. Progress in Hormone Res.* 38:511–556 (1982).

Larner, J. et al., "Rat Liver Insulin Mediator Which Stimulates Pyruvate Dehydrogenase Phosphatase Contains Galactosamine and D–Chiroinositol," *Biochem. Biophys. Res. Commun.* 151(3):1416–1426 (1988).

Larner, J. and Craig, J.W., "Urinary myo–Inositol–to–chiro–Inositol Ratios and Insulin Resistance," *Diabetes Care* 19(1):76–78 (1996).

Malchoff, C.D. et al., "A Putative Mediator of Insulin Action Which Inhibits Adenylate Cyclase and Adenosine 3',5'–Monophosphate–Dependent Protein Kinase: Partial Purification from Rat Liver: Site and Kinetic Mechanism of Action," *Endocrinology* 102(4):1327–1337 (1987).

Mato, J.M. et al., "Identification of a Novel Insulin–sensitive Glycophospholipid from H35 Hepatoma Cells," *J. Biol. Chem.* 262(5):2131–2137 (1987).

Mato, J.M. et al., "Partial Structure of an Insulin–sensitive Glycophospholipid," *Biochem. Biophys. Res. Commun.* 146(2): 764–770 (1987).

(List continued on next page.)

*Primary Examiner*—David Saunders
*Attorney, Agent, or Firm*—Sterne, Kessler, Goldstein & Fox P.L.L.C.

[57] ABSTRACT

The present invention provides a new method for screening for insulin resistance that utilizes both myoinositol and chiroinositol as indicators. According to this method, levels of myoinositol and D-chiroinositol are measured. The value of the concentration of myoinositol is divided by that of D-chiroinositol to give a "myo/chiro ratio." The value of this ratio is compared with a value that is characteristic of insulin resistance. If the characteristic value is equaled or exceeded, insulin resistance is indicated.

2 Claims, No Drawings

OTHER PUBLICATIONS

Messina, J.L. et al., "Positive Interaction between Insulin and Phorbol Esters on the Regulation of a Specific Messenger Ribonucleic Acid in Rat Hepatoma Cells," *Endocrinology* 121(4):1227–1232 (1987).

Ortmeyer, H.K. et al., "Chiroinositol Deficiency and Insulin Resistance. I. Urinary Excretion Rate of Chiroinositol Is Directly Associated with Insulin Resistance in Spontaneously Diabetic Rhesus Monkeys," *Endocrinology* 132(2):640–645 (1993).

Ortmeyer, H.K. et al., "Chiroinositol Deficiency and Insulin Resistance. II. Acute Effects of D–Chiroinositol Administration in Streptozotocin–Diabetic Rats, Normal Rats Given a Glucose Load, and Spontaneously Insulin–Resistant Rhesus Monkeys," *Endocrinology* 132(2):646–651 (1993).

Ostlund, Jr., R.E. et al., "D–chiro–Inositol Metabolism in diabetes mellitus," *Proc. Natl. Acad. Sci. USA* 90:9988–9992 (1993).

Romero, G. et al., "Phosphatidylinositol–Glycan Anchors of Membrane Proteins: Potential Precursors of Insulin Mediators," *Science* 240:504–511 (1988).

Romero, G. et al., "Anti–Inositol Antibodies Selectively Block Some of the Actions of Insulin in Intact $BC_3H1$ Cells," *Proc. Natl. Acad. Sci. USA* 87:1476–1480 (1990).

Saltiel, A.R. and Cuatrecasas, P., "Insulin stimulates the generation from hepatic plasma membranes of modulators derived from an inositol glycolipid," *Proc. Natl. Acad. Sci. USA* 83:5793–5797 (1986).

Sato, T. et al., "Contrasting Interactions between Phorbol Ester and Insulin on the Regulation of Glycogen Synthase Activity and p33 mRNA Accumulation in Rat Hepatoma Cells," *Arch. Biochem. Biophys.* 260(1):377–387 (1988).

Suzuki, S. et al., "ATP–$Mn^{2+}$ Stimulates the Generation of a Putative Mediator of Insulin Action," *J. Biol. Chem.* 262(7):3199–3204 (1987).

Suzuki, S. et al., "Urinary chiro–Inositol Excretion is an Index Marker of Insulin Sensitivity in Japanese Type II Diabetes," *Diabetes Care* 17:1465–1468 (1994).

Thompson, M.P. et al., "Purification and partial characterization of a putative member of insulin action on cyclic AMP–dependent protein kinase," *Mol. Cell. Biochem.* 62:67–75 (1984).

Williamson, J.R. et al., "Diabetes–Induced Increases in Vascular Permeability and Changes in Granulation Tissue Levels of Sorbitol, Myo–inositol, Chiro–inositol, and Scyllo–inositol Are Prevented by Sorbonil," *Metabolism* 35(4 Suppl. 1):41–45 (1986).

A.S. Kennington et al, New England Jour. Med., 323, 373–378, 1990.

METHOD FOR DETECTING INSULIN RESISTANCE

This application is a continuation-in-part of application Ser. No. 07/953,708, filed Sep. 30, 1992, now U.S. Pat. No. 5,427,956, which is a continuation of application Ser. No. 07/870,771, filed Apr. 21, 1992, now U.S. Pat. No. 5,183,764, now abandoned, which is a continuation of application Ser. No. 07/476,953, filed Feb. 8, 1990, now abandoned, which in turn is a continuation-in-part of application Ser. No. 07/320,485 filed Mar. 8, 1989, now abandoned.

FIELD OF THE INVENTION

This invention pertains to a quantitative assay for a marker or predictor of insulin resistance and of type II diabetes in mammals, specifically, a quantitative assay which provides for quick screening of individual patients for an indicator of insulin resistance, the absence of chiro-inositol. The assay provides a low-cost, quick method for conducting an assay for insulin resistance, or a predilection to the development of insulin resistance, in mammals, including humans.

BACKGROUND OF THE INVENTION

Insulin resistance is a disorder of glucose metabolism. Insulin resistant persons have a diminished ability to properly metabolize glucose and respond poorly, if at all, to insulin therapy. Insulin resistance can cause or contribute to hypertension, obesity, atherosclerosis and a variety of other disorders. Eventually, it can progress to a point where a diabetic state is reached. Insulin resistant (or Type II) diabetes is a severe and potentially disabling disorder if not properly treated.

New and effective methods of treating insulin resistance have recently been discovered. These treatment methods are useful in the treatment of insulin resistance even before the disorder manifests itself in the form of Type II diabetes. However, in order to take full advantage of these new treatment methods, an effective method of making an early identification of insulin resistant persons is required. It has already been reported that low levels of D-chiroinositol in blood or urine indicate the existence of insulin resistance. See Kennington, et al. v. *New England J. of Medicine*, Vol. 323 pp. 373-78 (1990) and Suzuki et al. in "New Direction in Clinical Research and Clinical Works for Obesity and Diabetes," pp. 197-203, Elsevier Science Pub. (1991).

However, it has been discovered that the effectiveness of identification can be affected by age, race, gender, sample volume and other factors. Accordingly, it remains an object of those of ordinary skill in the art to provide a sensitive, quantitative assay for insulin resistance or a predilection to the development of insulin resistance.

SUMMARY OF THE INVENTION

The above objects, and others more fully developed below, are achieved by the present invention.

The present invention provides a new method for screening for insulin resistance that utilizes both myoinositol and chiroinositol as indicators. This results in a more reliable, sensitive and discriminating method of screening for insulin resistance. According to this method, levels of myoinositol and D-chiroinositol are measured. The value of the concentration of myoinositol is divided by that of D-chiroinositol to give a "myo/chiro ratio." The value of this ratio is compared with a value that, is characteristic of insulin resistance. If the characteristic value is equaled or exceeded, insulin resistance is indicated.

DETAILED DESCRIPTION OF THE INVENTION

Methods for the measurement of inositols, such as GC-MS and RIA, are well known. See, Kennington et al. and Suzuki et al., supra.

Studies on Pima Indian populations of Arizona, as well as a patient population in and about the University of Virginia, Charlottesville, Va., and diabetic rhesus monkeys at the University of Maryland Primate Center, exhibit a virtual absence of chiro-inositol in diabetic individuals. The marked correlation between chiro-inositol concentrations and insulin-resistance, through these blind-blind studies, was particularly dramatic when compared with the concentrations of structurally related myo-inositol, which are generally elevated in diabetic patients, and were significantly higher in the diabetic subjects studied than non-diabetics.

Using GC-MS, the data presented in Tables 1 and 2 were collected. Table 1 presents data collected from a population in Central Virginia. Table 2 presents data obtained from a study of Pima Indians, a population in which there is a very high incidence of insulin resistance and Type II diabetes. The Virginia study includes data for relatives of known Type II diabetics, a group which is known to be at risk, for insulin resistance.

TABLE 1

Myoinositol and D-chiroinositol in Urine

|  | Myoinositol | D-chiroinositol | Myo/Chiro Ratio |
|---|---|---|---|
| Normal Population | 91 mg/ml | 36.1 mg/ml | 2.5 |
| Type II Diabetes | 270 mg/ml | 13.2 mg/ml | 20.4 |
| First Degree Relatives of Type II Diabetics | 90 mg/ml | 6.8 mg/ml | 13.2 |

TABLE 2

Myoinositol and D-chiroinositol in Urine of Pima Indians

|  | Myoinositol | D-chiroinositol | Myo/Chiro Ratio |
|---|---|---|---|
| Normal Population | 112 mg/ml | 52.3 mg/ml | 2.1 |
| Type II Diabetes | 244 mg/ml | 11.1 mg/ml | 22.0 |

The data is consistent with the observation that "normal" levels of myoinositol and D-chiroinositol vary between populations. Optimal use of these compounds as separate indicators of insulin resistance therefore requires that characteristic levels be set based on gender, age, race, time of sample collection, total daily urine output, and other factors. However, when one examines the myo/chiro ratios, the effects of these factors are greatly reduced and, to a large extent, they may be ignored.

The concentration of myoinositol and chiroinositol can be measured by any of several known techniques, such as GC-MS or RIA. Some of these techniques may be unequally sensitive to these two substances. Thus, the ratio values which are characteristic of normal and insulin resistant persons may appear to differ, depending on the analytical method used. However, this poses no obstacle to reliable testing, as long as an appropriate analytical method is consistently applied.

The data in Tables 1 and 2 show that ratio values of 5 or less may be generally regarded as normal. Values of 10 or more indicate at least a predisposition to insulin resistance, with higher values indicating possible Type II diabetes.

Thus, the present invention makes it possible to identify persons predisposed to insulin resistance, confirm a diagnosis of Type II diabetes, or to exclude a diagnosis of insulin resistance. All of this may be done on the basis of a single urine sample, uncorrected for total daily urine output or other factors.

It should be noted that this invention can be practiced through assays other than GC/MS. A wide variety of assays are known to those of ordinary skill in the art for the detection of specific compounds, and the use of any one which is consistent with a derivatized, dried or liquid sample is appropriate herein. Thus, enzyme reduction/oxidation potential measurements, using for example, an immobilized enzyme specific for chiro-inositol, the immobilized enzyme being in a fixed relationship to an electrode, may be used. The presence of chiro-inositol will result in the enzyme-catalyzed reaction going forward, altering the electrical environment detected by the electrode. Alternative assays that can be employed may include antibody assays, e.g., ELISA, LISA, RIA, agglutination assays and the like. All such assays are within the context of the invention claimed herein.

The above invention has been described with reference to specific examples and materials. It should be clear that these specifics can be varied without departing from the scope of the invention.

The invention will now be described by way of the following claims.

I claim:

1. A method for screening non-diabetic persons for insulin resistance, comprising the steps of (a) measuring the concentration of D-chiroinositol in a urine sample;

(b) measuring the concentration of myoinositol in a urine sample;

(c) calculating a ratio of myoinositol to D-chiroinositol; and (d) comparing the calculated ratio to a ratio that is characteristic of insulin resistance, wherein the non-diabetic person is determined to be likely to be insulin resistant if the calculated ratio exceeds the ratio that is characteristic of insulin resistance.

2. A method for identifying persons who are predisposed to insulin resistance, comprising the steps of (a) measuring the concentration of D-chiroinositol in a urine sample;

(b) measuring the concentration of myoinositol in a urine sample;

(c) calculating a ratio of myoinositol to D-chiroinositol; and (d) comparing the calculated ratio to a ratio that is characteristic of predisposition to insulin resistance, wherein the person is determined to be predisposed to insulin resistance if the calculated ratio exceeds the ratio that is characteristic of predisposition to insulin resistance.

* * * * *